(12) United States Patent
Natori (10) Patent No.: US 6,821,248 B2
(45) Date of Patent: Nov. 23, 2004

(54) LIFE SUPPORTING APPARATUS

(75) Inventor: Shuji Natori, Tokyo (JP)

(73) Assignees: Pioneer Design Corporation, Tokyo (JP); Pioneer Corporation, Tokyo (JP)

( * ) Notice: Subject to any disclaimer, the term of this patent is extended or adjusted under 35 U.S.C. 154(b) by 506 days.

(21) Appl. No.: 09/861,678

(22) Filed: May 22, 2001

(65) Prior Publication Data

US 2002/0004629 A1 Jan. 10, 2002

(30) Foreign Application Priority Data

May 29, 2000 (JP) .................................... P. 2000-158441

(51) Int. Cl.[7] .................................................. A61B 5/00
(52) U.S. Cl. ...................... 600/300; 600/485; 600/508; 128/920
(58) Field of Search ................................. 600/300, 481, 600/485, 508, 509, 301; 128/920, 903, 904

(56) References Cited

U.S. PATENT DOCUMENTS

| | | | | |
|---|---|---|---|---|
| 6,304,788 B1 | * | 10/2001 | Eady et al. | 600/300 |
| 6,319,207 B1 | * | 11/2001 | Naidoo | 600/300 |
| 6,398,729 B1 | * | 6/2002 | Levinson | 600/300 |
| 6,443,890 B1 | * | 9/2002 | Schulze et al. | 600/300 |
| 6,544,198 B2 | * | 4/2003 | Chong et al. | 600/300 |
| 6,602,191 B2 | * | 8/2003 | Quy | 600/300 |
| 6,648,820 B1 | * | 11/2003 | Sarel | 600/300 |

* cited by examiner

*Primary Examiner*—Fadi H. Dahbour
(74) *Attorney, Agent, or Firm*—Sughrue Mion, PLLC

(57) ABSTRACT

A display 2A, a CCD camera 2C, a speaker/microphone 2D, and service select pads 2Ga through 2Gd which are allotted to the life supporting services to be provided are disposed. As a life supporting service is selected by means of the service select pads 2Ga through 2Gd, the display 2A, the CCD camera 2C and the speaker/microphone 2D are connected to service providing facilities which provide the selected life supporting service, through a public telephone line network T or the Internet I.

24 Claims, 6 Drawing Sheets

LIFE SUPPORTING APPARATUS

BACKGROUND OF THE INVENTION

1. Technical Field of the Invention

The present invention relates to a device for supporting lives of aged people, handicapped people, etc.

2. Problems to be Solved by the Invention

Recently life styles have been changing through the use of various types of digital equipment as the information-oriented society has evolved. For instance, there are proposed various types of service providing systems for supporting life using a computer network, such as the Internet.

Such service providing systems for supporting life include, for instance, a vital monitoring system which monitors the condition of health of a subject of diagnosis who is far away from a medical institution.

However, when aged or handicapped people, for example, are to receive such services for supporting their lives, some people find it very difficult to manipulate an advanced information/network terminal, such as a personal computer, and use the Internet or the like.

This leads to a digital divide between people who can operate an advanced information/network terminal, such as a personal computer, and people who can not operate an advanced information/network terminal. Therefore, there is a problem that those who can not operate digital equipment can not fully access such support in their lives which use otherwise helpful information networks.

Such a problem is frequent among old people who particularly need supports in their lives, which is thought to be a worsening problem with the progressive aging of society.

The present invention has been made to solve the digital divide problem in the support of people's lives as described above.

More precisely, the present invention aims at allowing even those people who are not familiar with how to operate an information/network terminal, such as a personal computer, to easily use an information network-based life supporting system, and hence expand the network distribution business.

SUMMARY OF THE INVENTION

[Means for Solving the Problems]

To achieve the above object, a life supporting device according to the first aspect of the invention comprises an image display member, an imaging member, a recording member, a voice output member, and service selection members allocated to each life supporting service which is to be provided, and is characterized in that as life supporting services are selected by operating said service selection member, said image display member, said imaging member, said recording member and said voice output member become connected to service providing facilities which provide selected life supporting services through a telecommunications line or a computer network.

The life supporting device according to the first aspect of the invention can be installed in a public space, such as an old people's center, a nursing home for the aged and a care house, where people who are in need of support such as the elderly and handicapped people gather, or can be installed in a home.

The life supporting device is connected to service providing facilities, such as a medical service center and an Internet site which provides various types of on-line services, through a public telephone line network, and a computer network such as the Internet, or the like.

When a user who wishes to use the life supporting device tries to receive various types of on-line life supporting services, the user first selects a desired life supporting service using the service selection member.

This connects the image display member, the imaging member, the recording member, the voice output member which are disposed to the life supporting device to service providing facilities which provide the desired selected life supporting service through a public telephone line network, a computer network such as the Internet, or the like, thereby making it possible to transmit and receive information to and from the service providing facilities.

Image data transmitted from the service providing facilities are displayed by the imaging member, voice data similarly transmitted from the service providing facilities are outputted from the voice output member, or video data imaged with the imaging member or voices recorded by the recording member are transmitted to the service providing facilities, whereby various types of life supporting services, such as medical services including medical checkup and doctors' inquiries, counseling services, communication supporting services and entertainment services, using the image display member, the imaging member, the recording member and the voice output member.

As described above, according to the first aspect of the invention, a user, even someone who is not familiar with how to operate an information/network terminal such as a personal computer, or an aged person who particularly needs supports to his or her life, etc., is required only to select a desired life supporting service using the service selection members in order to be connected to service providing facilities which provide the desired life supporting service, resulting in easy access to such services.

The digital divide is therefore narrowed, which in turn makes it easy particularly for the aged and the like to use a life supporting system on an information network, and hence, allows the network distribution business to expand.

To achieve the above object, a life supporting device according to the second aspect of the invention is characterized in further comprising, in addition to the structure according to the first aspect of the invention, a data reader member which reads recorded data which are recorded in a recording medium from said recording medium, and becomes connected to service providing facilities which are selected by operating said service selection member so as to transmit said recorded data read from said recording medium to said service providing facilities to which said data reader member are connected.

As a user selects a desired life supporting service using the service selection member, said data reader member of the life supporting device according to the second aspect of the invention, together with the image display member, the imaging member, the recording member and the voice output member, becomes connected to service providing facilities which provide the desired selected life supporting service through a public telephone line network, a computer network such as the Internet, or the like, whereby it becomes possible to communicate with the service providing facilities.

This makes it possible to easily transmit to the service providing facilities data for receiving the life supporting service which have been recorded in a recording medium in advance.

When a user uses the medical checkup service, or medical services based on doctor's inquiries to patients, or the like provided by a medical institution or the like using this life supporting device, for example, the data reader member such as an IC card reader reads vital data such as electrocardiogram data regarding the user which are recorded in a recording medium such as an IC card, from this recording medium and transmits the vital data to a connected medical institution or the like, so that the user can easily receive medical services such as a medical checkup.

To achieve the above object, a life supporting device according to a third invention is characterized in further comprising, in addition to the structure according to the first aspect of the invention, a printing member which becomes connected to service providing facilities which are selected by operating said service selection members so as to print the contents of data which are transmitted from said service providing facilities to which said printing member are connected.

As a user selects a desired life supporting service using the service selection member, said printing member of the life supporting device according to the third invention, together with the image display member, the imaging member, the recording member and the voice output member, becomes connected to service providing facilities which provide the desired selected life supporting service through a public telephone line network, a computer network such as the Internet, or the like, whereby it becomes possible to communicate with the service providing facilities.

This allows data contents or the like which are provided from the connected service providing facilities, for example, to be printed and provided to the user.

To achieve the above object, a life supporting device according to the fourth aspect of the invention is characterized in further comprising, in addition to the structure according to the first aspect of the invention, an image input member which scans and reads an image and becomes connected to service providing facilities which are selected by operating said service selection members so as to transmit image data which are read to said service providing facilities to which said image input member are connected.

As a user selects a desired life supporting service using the service selection member, said image input member of the life supporting device according to the fourth aspect of the invention, together with the image display member, the imaging member, the recording member and the voice output member, becomes connected to service providing facilities which provide the desired selected life supporting service through a public telephone line network, a computer network such as the Internet, or the like, whereby it becomes possible to communicate with the service providing facilities.

In consequence, a material prepared in writing for receiving services is read and transmitted by said image input member to the service providing facilities, which make it easy for the user to receive services provided by the service providing facilities.

To achieve the above object, a life supporting device according to the fifth aspect of the invention is characterized in further comprising, in addition to the structure according to the first aspect of the invention, a vital data detection member which detects vital data and becomes connected to service providing facilities which are selected by operating said service selection members so as to transmit vital data, which are detected, to said service providing facilities to which said vital data detection member are connected.

As a user selects a desired life supporting service using the service selection member, said vital data detection member of the life supporting device according to the fifth aspect of the invention, together with the image display member, the imaging member, the recording member and the voice output member, becomes connected to service providing facilities which provide the desired selected life supporting service through a public telephone line network, a computer network such as the Internet, or the like, whereby it becomes possible to communicate with the service providing facilities.

This connects, when the user selects medical services, for example, said vital data detection member to a medical institution or the like which provides medical services. The vital data detection member transmits detected vital data, such as the heart rate, pulse and blood pressure, regarding the user to the medical institution or the like, and the vital data are used as materials for a medical checkup, etc.

To achieve the above object, a life supporting device according to the sixth aspect of the invention is characterized in further comprising, in addition to the structure according to the first aspect of the invention, a cursor movement control member which moves a cursor on a computer screen which is displayed on said display member.

In the life supporting device according to the sixth aspect of the invention, during execution of a life supporting service provided from a service providing facilities on a computer screen which is displayed on said display member, movements of a cursor on the computer screen are manipulated by the cursor movement control member.

To achieve the above object, a life supporting device according to the seventh aspect of the invention is characterized in that, in addition to the structure according to the first aspect of the invention, there are a plurality of such service selection members corresponding to category of life supporting services to be provided.

In the life supporting device according to the seventh aspect of the invention, as a user merely selects and operates the service selection members to which a desired life supporting service is allocated, the life supporting device is connected to service providing facilities which provide the desired life supporting service. Hence, even an aged person or the like who is not familiar with how to operate an information/network terminal can easily select the life supporting service and get connected to the service providing facilities.

To achieve the above object, a life supporting device according to the eighth aspect of the invention is characterized in that, in addition to the structure according to the seventh aspect of the invention, said plurality of service selection members are colored differently from each other.

In the life supporting device according to the eighth aspect of the invention, since the service selection members are colored differently from each other in accordance with categories of life supporting services, it is possible to select a desired life supporting service in an easy manner.

To achieve the above object, a life supporting device according to the ninth aspect of the invention is characterized by further comprising, in addition to the structure according to the first aspect of the invention, a motion command member which performs image analysis on the motion of a person which is shot with said imaging member, compares this with previously set motion patterns, and outputs a predetermined operation signal, which corresponds to a motion pattern which matches the captured motion of the person, to said imaging member, said recording member, said voice output member or said service selection members.

With respect to the life supporting device according to the ninth aspect of the invention, when a user makes a predetermined motion with signs and gestures, etc., the motion command member performs image analysis on a video signal which is obtained from the motion which is shot by the imaging member. When the motion matches with a predetermined motion pattern, in response to the operation signal outputted from the motion command member, the imaging member, the recording member, the voice output member or the service selection members performs an operation which corresponds to the motion pattern.

To achieve the above object, a life supporting device according to the tenth aspect of the invention is characterized in further comprising, in addition to the structure according to the first aspect of the invention, a voice command member which analyzes a voice which is recorded with said recording member, compares this with previously set voice patterns, and outputs a predetermined operation signal, which corresponds to a voice pattern which matches with the recorded voice, to said imaging member, said recording member, said voice output member or said service selection member.

With respect to the life supporting device according to the tenth aspect of the invention, when the user makes a predetermined pronouncement, the voice command member analyzes the voice signal of the voice recorded by the recording member. When the voice matches with a predetermined voice pattern, in response to the operation signal outputted from the voice command member, the imaging member, the recording member, the voice output member or the service selection members performs an operation which corresponds to the voice pattern.

To achieve the above object, a life supporting device according to the eleventh aspect of the invention is characterized in that, in addition to the structure according to the first aspect of the invention, an armrest member for supporting a human arm is attached in front of an operation panel in which said image display member, said imaging member, said recording member, said voice output member and said service selection members are arranged.

Using the life supporting device according to the eleventh aspect of the invention, since it is possible to support a user's body as the user leans against the armrest member, the user can easily manipulate the life supporting device even when the user is aged or handicapped.

To achieve the above object, a life supporting device according to the twelfth aspect of the invention is characterized in that, in addition to the structure according to the first aspect of the invention, an operation panel in which said image display member, said imaging member, said recording member, said voice output member and said service selection members are arranged is disposed on a supportive base which is approximately as tall as a table.

Since the life supporting device according to the twelfth aspect of the invention allows a user to operate the operation panel in which said image display member, said imaging member, said recording member, said voice output member and said service selection member are arranged, while sitting in a chair, even an aged or handicapped person can operate the life supporting device whilst assuming a comfortable posture.

To achieve the above object, a life supporting device according to the thirteenth aspect of the invention is characterized in that, in addition to the structure according to the first aspect of the invention, said service providing facilities include medical service facilities, and medical services are provided through said image display member, said imaging member, said recording member and said voice output member by means of a connection with said medical service facilities. Hence, a user can receive medical services such as medical checkup and face-to-face diagnosis using a videophone.

To achieve the above object, a life supporting device according to the fourteenth aspect of the invention is characterized in that, in addition to the structure according to the first aspect of the invention, said service providing facilities include facilities which provide services regarding counseling. Hence, a user can receive life supporting services such as advice regarding their life.

To achieve the above object, a life supporting device according to the fifteenth aspect of the invention is characterized in that, in addition to the structure according to the first aspect of the invention, said service providing facilities include facilities which provide surrogate services for civic procedures. Hence, by deputizing someone to do civic procedures at a municipal office and the like, a user can receive supports to his or her daily life.

To achieve the above object, a life supporting device according to the sixteenth aspect of the invention is characterized in that, in addition to the structure according to the first aspect of the invention, said service providing facilities include facilities which provide services as a travel agency. Hence, a user can receive life supporting services such as to be introduced a package tour and to arrange a journey.

To achieve the above object, a life supporting device according to the seventeenth aspect of the invention is characterized in that, in addition to the structure according to the first aspect of the invention, said service providing facilities include facilities which provide a service to introduce someone for conversation. Hence, a user can easily find opportunities to communicate.

To achieve the above object, a life supporting device according to the eighteenth aspect of the invention is characterized in that, in addition to the structure according to the first aspect of the invention, said service providing facilities include facilities which provide the service of sending e-mail. Hence, even an aged person or the like who is not familiar with how to operate an information/network terminal can easily use e-mails.

To achieve the above object, a life supporting device according to the nineteenth aspect of the invention is characterized in that, in addition to the structure according to the first aspect of the invention, said service providing facilities include facilities which provide the service of translating letters. Hence, even an aged person can easily write a letter directed to a foreign country or easily read a letter received from a foreign country.

To achieve the above object, a life supporting device according to the twentieth aspect of the invention is characterized in that, in addition to the structure according to the first aspect of the invention, said service providing facilities include facilities which provide the service of drawing composite sketches. Hence, a user's face is synthesized into a past face, a future face, a CG character-like or an animated cartoon-like face, etc., from data obtained by actually shooting the face with the imaging member.

To achieve the above object, a life supporting device according to the twenty-first aspect of the invention is characterized in that, in addition to the structure according to the first aspect of the invention, said service providing facilities include facilities which provide game services. Hence, various types of games, such as a game for the aged, are provided.

To achieve the above object, a life supporting device according to the twenty-second aspect of the invention is characterized in that, in addition to the structure according to the first aspect of the invention, said service providing facilities include facilities which provide services regarding printed matter. Hence, various types of printed matter, such as printed cards describing the lyrics of karaoke songs and colored paper printed with lines indicating the places to fold for making figures by folding, are provided.

DETAILED DESCRIPTION OF THE PREFERRED EMBODIMENTS

[Preferred Embodiments of the Invention]

In the following, most preferred embodiments of the present invention will be described with reference to the associated drawings.

Figure 1:
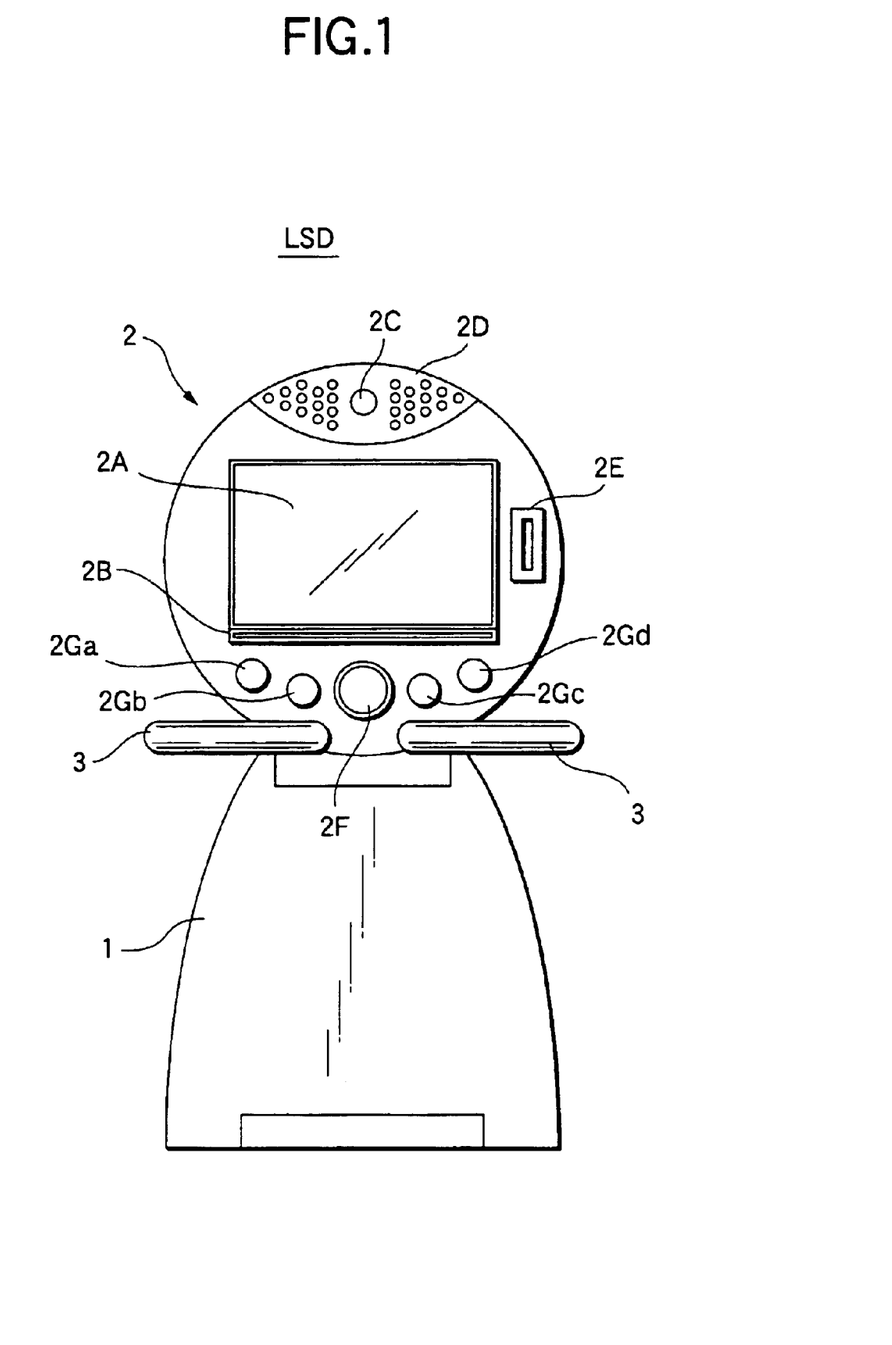
FIG. 1 is a front view showing one example according to a preferred embodiment of the present invention.

FIG. 1 shows an example of a life supporting device according to a preferred embodiment of the present invention.

In FIG. 1, the life supporting device (LSD) is such that an operation part 2 is mounted on a supportive base 1 which is approximately as tall as a table.

An armrest 3 for supporting an aged person's body while the aged person or the like operates the life supporting device (LSD) is attached between the base part 1 and the operation part 2 such that the armrest 3 protrudes at both sides towards the front.

A display 2A for showing a videophone image and displaying a computer screen is attached to a central portion of a panel of the operation part 2 of the life supporting device (LSD), and a color scanner/printer 2B, which reads a document, transmits thus read information through a telecommunications line and prints out various types of information which is transmitted through a telecommunications line, is attached in such a manner that a paper feed slot and a paper discharge slot are positioned horizontally along a bottom edge portion of the display 2A.

A CCD camera 2C, which shoots a user who is seated in front of the life supporting device (LSD) and transmits a corresponding video signal through a telecommunications line, is attached at a upper central position of the display 2A. A speaker/microphone 2D is disposed which converts the voice of a user, who is seated in front of the life supporting device (LSD), into a voice signal and thereafter transmits through a telecommunications line or converts a transmitted voice signal into a voice and thereafter outputs the signal. An IC card reader 2E is disposed such that an IC card insertion slot is positioned on the right-hand side of the display 2A as a user faces it.

Further, a joymouse/vital sensor 2F, which comprises, as an integrated part, a vital sensor which detects vital data, such as a heart rate, pulses and a blood pressure, from a joymouse for playing games and a user's hand which is in contact with the joymouse, is attached below the central position of the display 2A. In addition, on both sides of the joymouse/vital sensor 2F, a plurality of (four in this example) service select pads 2Ga through 2Gd are disposed which are for selecting various types of services which are provided by the life supporting device (LSD).

The joymouse/vital sensor 2F also serves as a cursor operation part for moving a cursor on a computer screen which is displayed on the display 2A.

The service select pads 2Ga through 2Gd are colored differently from each other so as to make it easy for the aged or the like to distinguish services which are allocated to the respective service select pads 2Ga through 2Gd, as described later.

Figure 2:
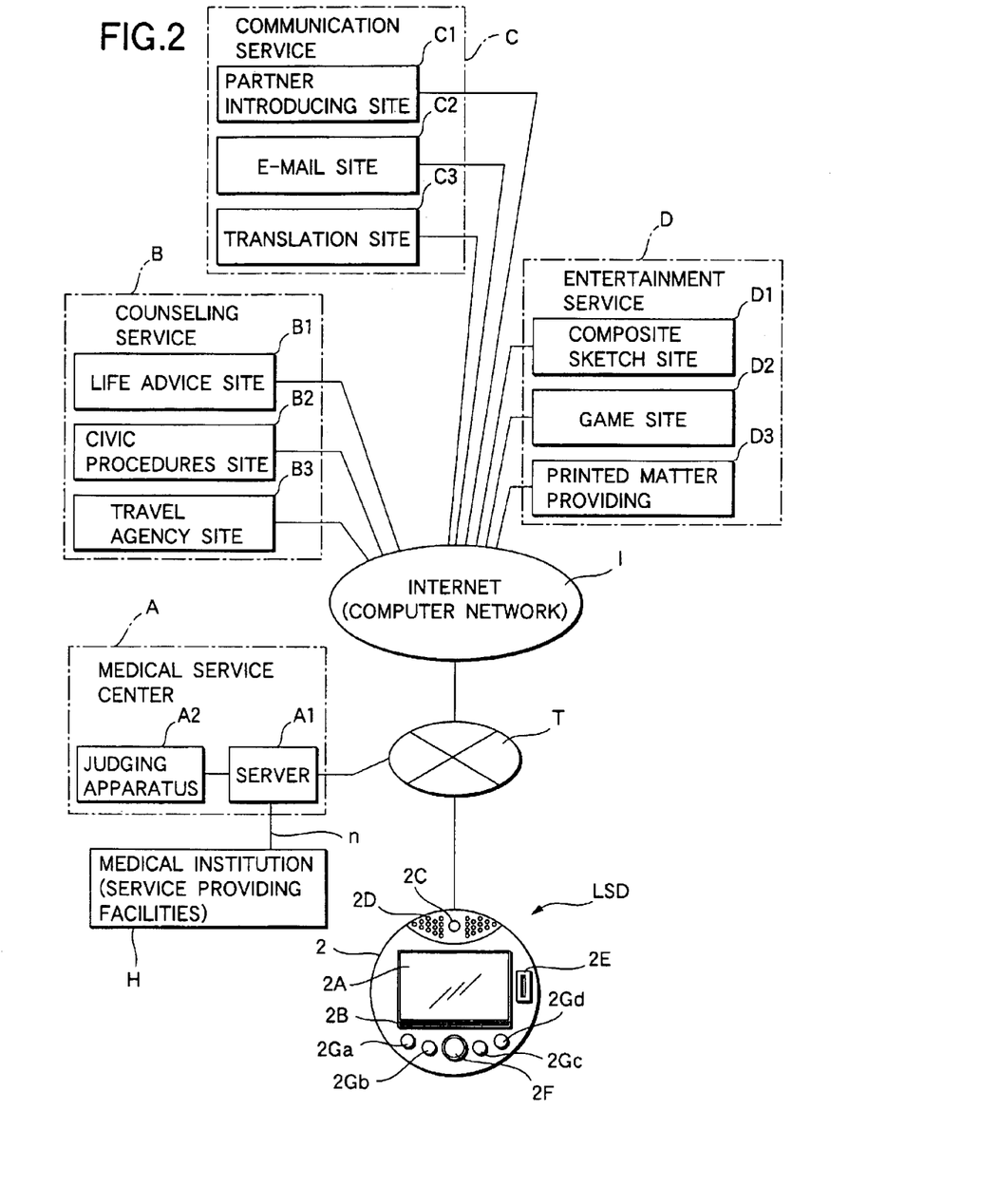
FIG. 2 is a network configuration diagram showing connection with service providing facilities in the same example.

The life supporting device (LSD) is connected to a public telephone line network T as shown in FIG. 2, and further to a medical service center A as that described later and the Internet I through the public telephone line network T.

Connected to the Internet I are life advice site B1, a civic procedures site B2 and a travel agency site B3 which belong to a counseling service genre B for various types of counseling and surrogate services for a user of the life supporting device (LSD), a conversation partner introducing site C1, e-mail site C2 and a translation site C3 which belong to a communication service genre C for auxiliary services for a user to communicate with other user, and a composite sketch site D1, a game site D2 and a printed matter providing site D3 which belong to an entertainment service genre D for providing entertainment to a user.

A server A1 for accumulating vital data regarding the subject of diagnosis (user of the life supporting device (LSD)) and a judging apparatus A2 which is connected with the server A1 are installed in the medical service center A. The judging apparatus A2 judges the condition of health of the subject of diagnosis based on the vital data regarding the subject of diagnosis supplied from the server A1, as described later.

Further, the server A1 is connected to a medical institution H, such as a hospital, through a telecommunications line n.

The life advice site B1 of the counseling service genre B is a site which provides advice for problems or the like that a user is faced with by means of dialogue, questionnaires, etc.

The civic procedures site B2 is a site which provides with a user surrogate services regarding civic procedures.

The travel agency site B3 is a site which presents package tours and the like and provides a user with the service to complete procedures for a journey.

The conversation partner introducing site C1 of the communication service genre C is a site which provides a service to introduce someone for conversation, etc.

The e-mail site C2 is a site which converts a hand-written letter or speech, which a user enters into the life supporting device (LSD), into an e-mail and transmits the e-mail.

The translation site C3 is a site which provides a service to translate a hand-written letter or speech which a user enters into the life supporting device (LSD) into English or the like and translating a letter, etc., received from a foreign country.

The composite sketch site D1 belonging to the entertainment service genre D is a site which provides a service to synthesize a user's face into a past or future face, a CG character-like or an animated cartoon-like face, etc., from data obtained by actually shooting the face.

The game site D2 is a site which provides various types of games, such as games intended for the aged.

The printed matter providing site D3 is a site which provides various types of printed matter, such as printed cards describing the lyrics of karaoke songs and colored paper printed with lines indicating the places to fold for making figures by folding.

The service select pad 2Ga of the operation part 2 of the life supporting device (LSD) is allocated with a function to connect the life supporting device (LSD) to the medical service center A. With the service select pad 2Ga pressed, the life supporting device (LSD) is connected with the medical service center A through the public telephone line network T.

As the life supporting device (LSD) is connected with the medical service center A, the IC card reader 2E transmits to the medical service center A personal medical chart data regarding a user read from an IC card inserted into the IC card reader 2E, and transmits to the medical service center A vital data, such as the heart rate, pulse and blood pressure to be detected from a user's hand which is in contact with the joymouse/vital sensor 2F.

After connection with the medical service center A, the life supporting device (LSD) is connected further with the medical institution H through the medical service center A as described later, so that the display 2A, the CCD camera 2C and the speaker/microphone 2D transfers and receives video signals and a voice signal with the medical institution H.

Further, the color scanner/printer 2B transfers and receives print data with the medical service center A and the medical institution H.

The service select pad 2Gb is allocated with a function to connect the life supporting device (LSD) to the respective sites of the counseling service genre B. With the service select pad 2Gb pressed repeatedly, the life supporting device (LSD) is connected sequentially with the sites B1 through B3 belonging to the counseling service genre B through the Internet I and the public telephone line network T.

The service select pad 2Gc is allocated with a function to connect the life supporting device (LSD) to the respective sites of the communication service genre C. With the service select pad 2Gc pressed repeatedly, the life supporting device (LSD) is connected sequentially with the sites C1 through C3 belonging to the communication service genre C through the Internet I and the public telephone line network T.

The service select pad 2Gd is allocated with a function to connect the life supporting device (LSD) to the respective sites of the entertainment service genre D. With the service select pad 2Gd pressed repeatedly, the life supporting device (LSD) is connected sequentially with the sites D1 through D3 belonging to the entertainment service genre D through the Internet I and the public telephone line network T.

As the life supporting device (LSD) is connected with any site through the Internet I, the display 2A shows a service providing screen for providing life supporting services which are available at the connected site.

Entries for receiving services are made in the service providing screen which is displayed by the display 2A, as the joymouse/vital sensor 2F is manipulated, the color scanner/printer 2B reads, the CCD camera 2C captures images, or the speaker/microphone 2D captures voices.

Services are provided from each connected site, by means of the display 2A to display a screen which shows the contents of the services or the color scanner/printer 2B to print out.

One can make basic operations on this life supporting device (LSD) or basic operations in a home page which are displayed by the display 2A, even using his or her voice, gestures and signs, which serve as voice/motion commands, through the CCD camera 2C and the speaker/microphone 2D.

Figure 3:
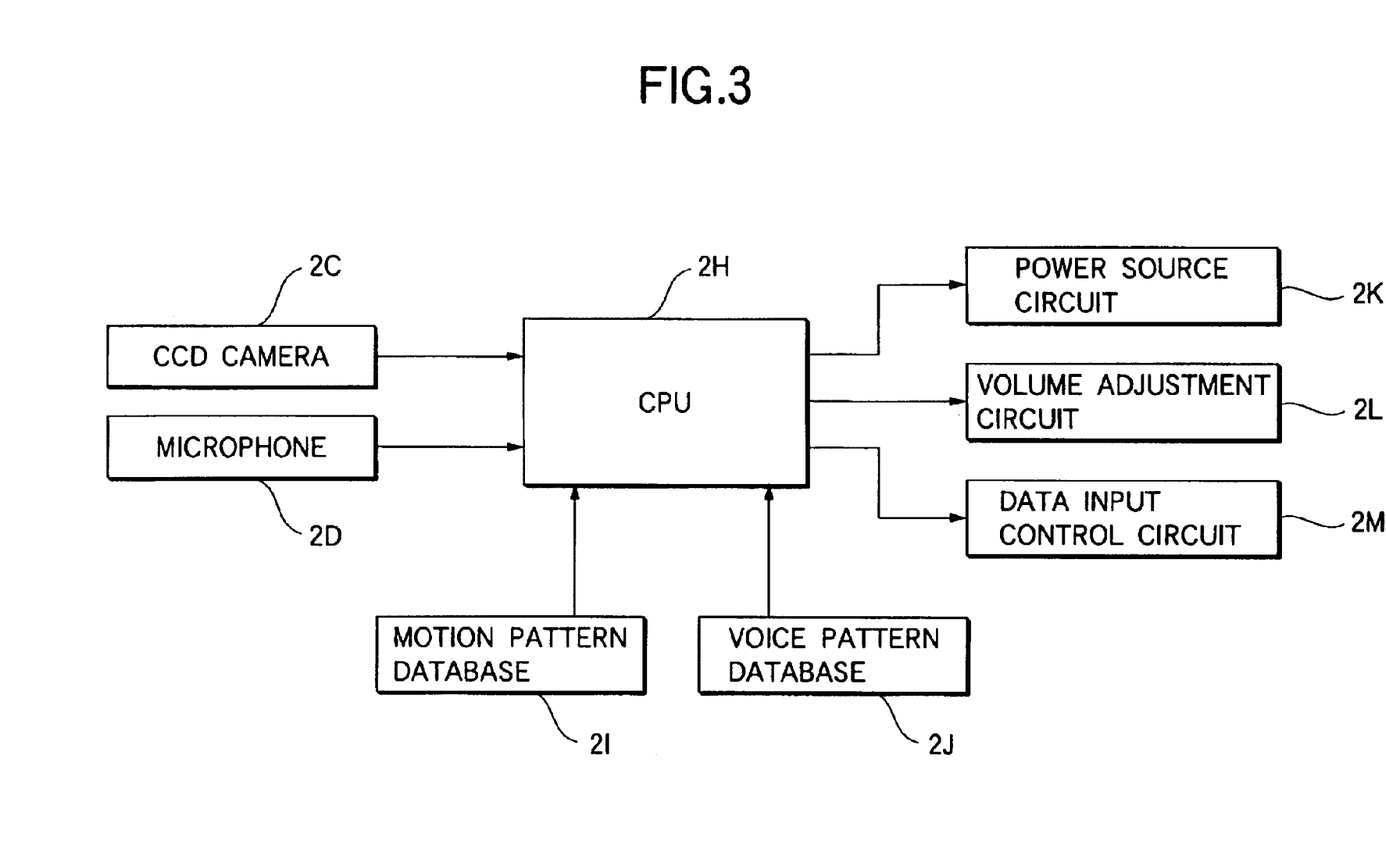
FIG. 3 is a block diagram showing the configuration of a voice/motion command in the example.

More precisely, as shown in FIG. 3, as the CCD camera 2C captures the user's motions such as gestures and signs, a video signal representing them is fed to a CPU 2H which is incorporated in the operation part 2. The CPU 2H compares, by means of image analysis, motion patterns stored in a motion pattern data base 2I with the user's motion expressed by the video signal. When the user's motion expressed by the video signal is found to match with a motion pattern stored in the motion pattern database 2I as a result, an operation instructing signal corresponding to this motion pattern is outputted to a power source circuit 2K or a volume adjustment circuit 2L and a data input control circuit 2M, whereby a power source is turned on or off, the volume is adjusted, data are entered, or other corresponding operations are made.

Meanwhile, when a user's voice is entered via the speaker/microphone 2D, a voice signal representing it is supplied to the CPU 2H. The CPU 2H compares voice patterns stored in a voice pattern database 2J with the user's voice expressed by the voice signal. When the user's voice expressed by the voice is found to match with a voice pattern stored in the voice pattern database 2I as a result, an operation instructing signal corresponding to this voice pattern is outputted to the power source circuit 2K or the volume adjustment circuit 2L and the data input control circuit 2M, whereby the power source is turned on or off, the volume is adjusted, data are entered, or other corresponding operations are made.

The life supporting device (LSD) described as above can be installed in a public space, such as an old people's center, a nursing home for the aged and a care home, where people, who are in need of support such as aged people and handicapped people, gather, or can be installed in a home.

Figure 4:
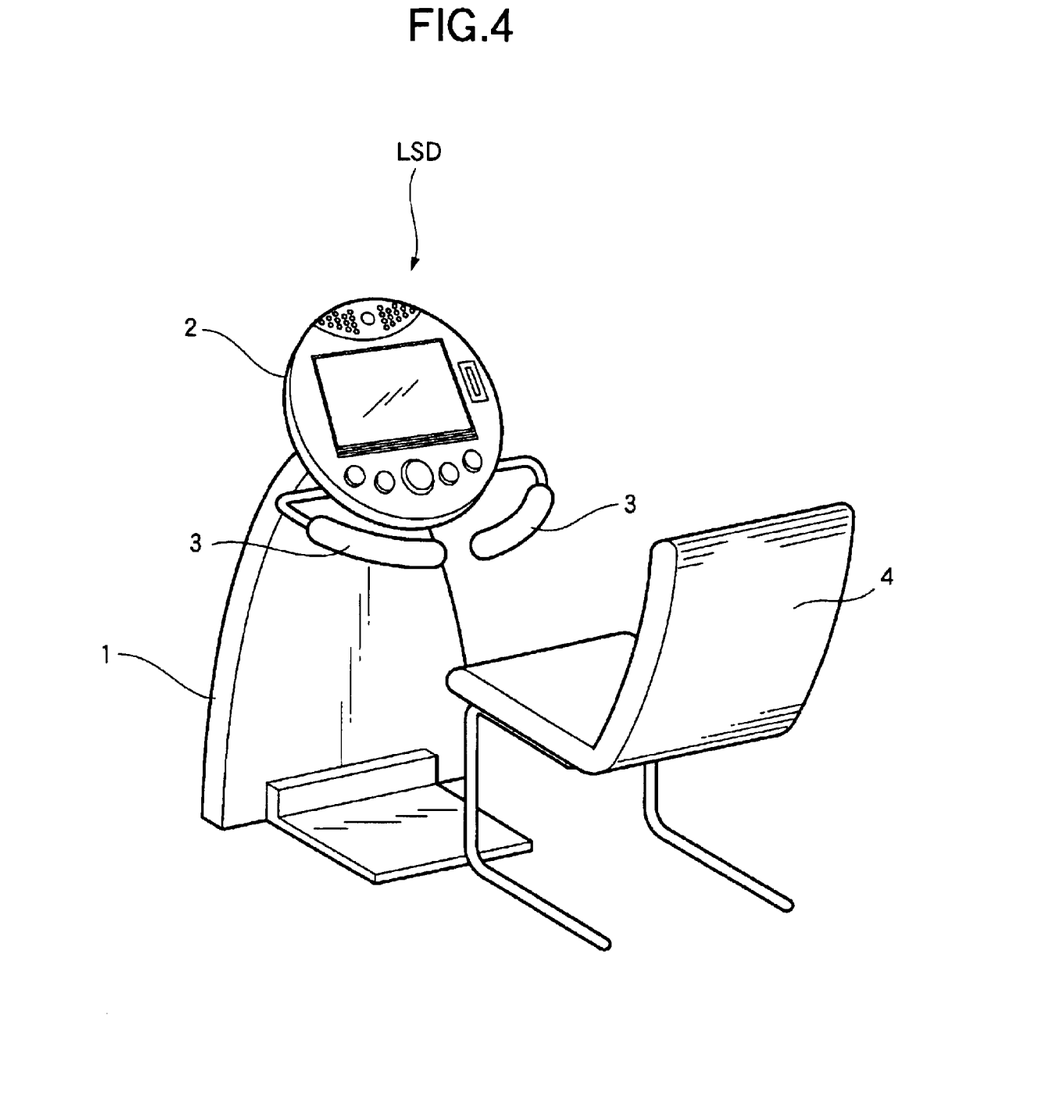
FIG. 4 is a perspective view of the life supporting device in the example.

Since the operation part 2 is mounted on the supportive base 1 which is approximately as tall as a table, a user who intends to use this life supporting device (LSD), can manipulate the operation part 2 while seated in a chair 4 which is placed in front of the life supporting device (LSD), as shown in FIG. 4.

An aged person or the like, in particular, can support his or her body with his or her arm rested on the arm rest 3 while manipulating the operation part 2, and therefore, it is easy to manipulate the life supporting device (LSD).

When a user wishes to receive various types of on-line services using this life supporting device (LSD), the user first selects any one of the service select pads 2Ga through 2Gd and presses the service select pad to which the desired service is allocated, to thereby choose the service.

For example, when a user wishes for the medical checkup or a medical inquiry service, as the service select pad 2Ga is pressed, the life supporting device (LSD) becomes connected with the medical service center A through the public telephone line network T.

As the user thereafter inserts an IC card which stores vital data, such as electrocardiogram data, prepared in advance into the IC card reader 2E, the IC card reader 2E reads the user's vital data from the IC card and transmits this to the medical service center A.

Further, as the user touches the joymouse/vital sensor 2F by hand, the joymouse/vital sensor 2F detects user's vital data, such as the heart rate, pulse and blood pressure, on the spot and transmits the data to the medical service center A.

At the medical service center A, the vital data transmitted from the life supporting device (LSD) as described above are accumulated together with a user's ID in the server A1 and fed to the judging apparatus A2.

The judging apparatus A2 judges a user's health condition based on the vital data which are supplied from the server A1.

When the judging apparatus A2 judges that a further examination is necessary, the server A1 is provided with imaging information, such as the user's face imaged with the CCD camera 2C which is mounted to the life supporting device (LSD), and the user's voice recorded with the speaker/microphone 2D, and the judging apparatus A2, whilst considers such additional information, judges the user's condition of health in more detail.

These judgment results are displayed on the display 2A or printed with the color scanner/printer 2B based on judgment data which indicate the judgment results which are transmitted to the life supporting device (LSD) from the medical service center A, whereby the user who is the subject of diagnosis is informed of the judgment results.

Further, with respect to a judgment result made at the medical service center A, when it is determined that a further inquiry is necessary or when the user wishes further inquiry, the life supporting device (LSD) is connected with the medical institution H, such as a hospital, through the server A1 of the medical service center A.

Figure 5:
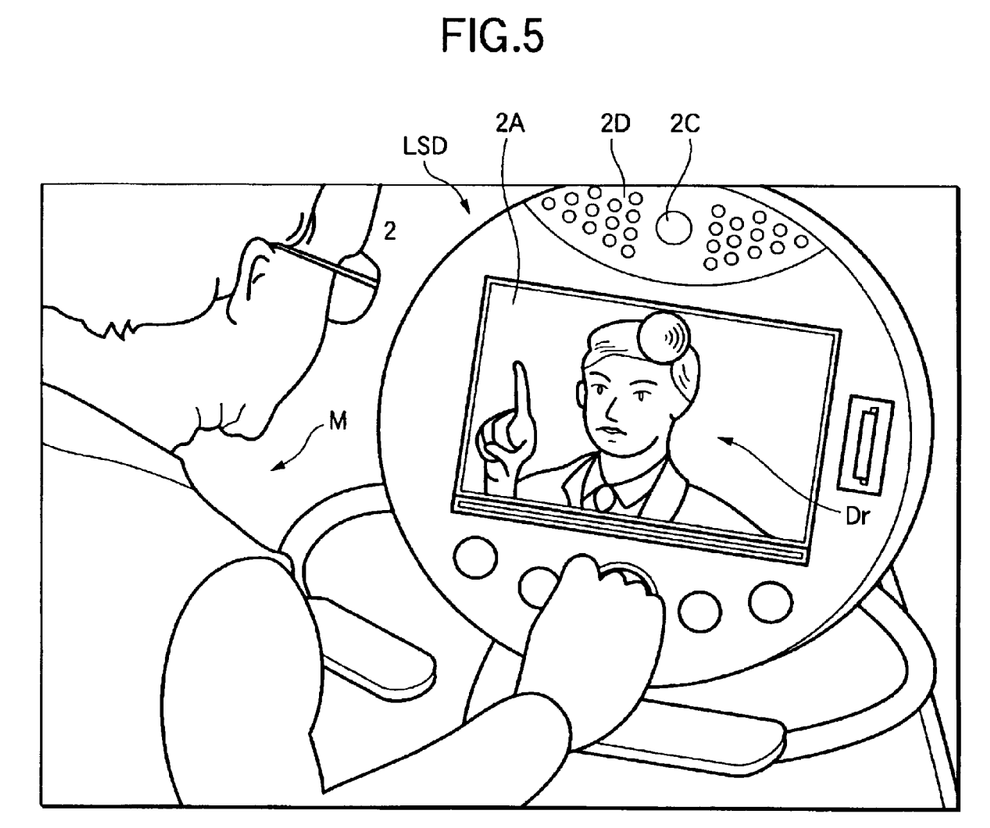
FIG. 5 is a scenery view for describing an embodiment of medical services in the example.

As shown in FIG. 5, an image of a user M captured with the CCD camera 2C and a voice recorded with the speaker/microphone 2D are transmitted to the medical institution H. In the life supporting device (LSD), the display 2A displays an image of a doctor Dr who is in the medical institution H and the speaker/microphone 2D outputs a voice of the doctor Dr, so that the user M can receive face-to-face examination using a videophone, and hence, receive a more correct diagnosis from the doctor Dr.

When a user hopes to receive a service which is classified as the counseling service genre B, as the service select pad 2Gb is pressed, the life supporting device (LSD) becomes connected with the respective sites B1 through B3 belonging to the counseling service genre B through the Internet I and the public telephone line network T. When a service which is classified as the communication service genre C is wished, as the service select pad 2Gc is pressed, the life supporting device (LSD) is connected with the respective sites C1 through C3 of the communication service genre C When a service which is classified as the entertainment service genre D, as the service select pad 2Gd is pressed, the life supporting device (LSD) is connected with the respective sites D1 through D3 of the entertainment service genre D.

At this stage, every time the service select pad 2Gb, 2Gc or 2Gd is pressed, the connection is switched from the life advice site B1 to the civic procedures site B2 and further to the travel agency site B3, or from the conversation partner introducing site C1 to the e-mail site C2 and further to the translation site C3, or from the composite sketch site D1 to the game site D2 and further to the printed matter providing site D3, and therefore, the user, by repeatedly pressing the service select pad 2Gb, 2Gc or 2Gd until getting connected to a site which provides a desired service, can easily select the desired service site.

In the case of the e-mail site C2 and the translation site C3 which require input of a hand-written document, as a user inserts a document to be inputted into the color scanner/printer 2B of the operation part 2, the color scanner/printer 2B reads the content of the document and the data thus read are transmitted to a service site to which the life supporting device (LSD) is connected.

Further, in the case of the composite sketch site D1 which requires a user's image, a user's image captured with the CCD camera 2C is transmitted to a service site to which the life supporting device (LSD) is connected.

Further, in the case of the composite sketch site D1 and the printed matter providing site D3 which provide services in writing, services (such as composite sketches, cards describing the lyrics of karaoke songs, and colored paper printed with lines indicating the places to fold for making figures by folding) are printed by the color scanner/printer 2B based on service data transmitted from service sites.

Further, the joymouse/vital sensor 2F realizes the operation of game software or the like provided from the game site D2.

Figure 6:
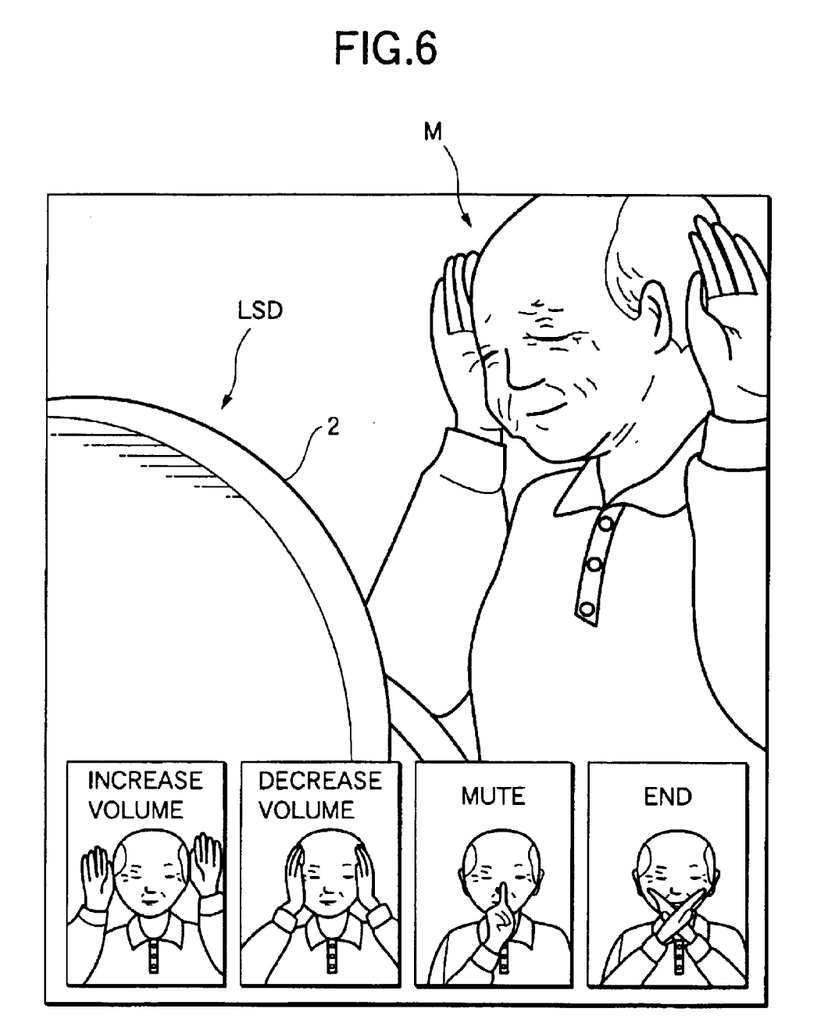
FIG. 6 is a scenery view for describing an embodiment of a voice/motion command in the example.

As shown in FIG. 6, the user M can use voice/motion commands which are created as the CCD camera 2C captures the motion of the user M and the speaker/microphone 2D records a voice of the user M as described above, in order to realize basic operations, such as to adjust a volume of the speaker/microphone 2D, and basic data input operations for various types of services on the Internet.

What is claimed is:

1. A life supporting device, comprising:

a recording member;

service selection members respectively allocated to each life supporting service which is to be provided; and a data reader member which reads recorded data, which are recorded in a recording medium, from said recording member, and is connected to service providing facilities which are selected by operating said service selection members so as to transmit said recorded data read from said recording medium to said service providing facilities to which said data reader member are connected.

2. A life supporting device, comprising:

an imaging member;

a recording member;

a voice output member;

service selection members respectively allocated to each life supporting service which is to be provided; and a motion command member which performs image analysis on the motion of a person which is shot with said imaging member, compares thereof with previously set motion patterns, and outputs a predetermined operation signal, which corresponds to a motion pattern which matches with the captured motion of the person, to said imaging member, said recording member, said voice output member or said service selection members.

3. A life supporting device, comprising:

an imaging member;

a recording member;

a voice output member;

service selection members respectively allocated to each life supporting service which is to be provided; and a voice command member which analyzes a voice which is recorded with said recording member, compares thereof with previously set voice patterns, and outputs a predetermined operation signal, which corresponds to a voice pattern which matches with the recorded voice, to said imaging member, said recording member, said voice output member or said service selection members.

4. A life supporting device, comprising:

an image display member, an imaging member, a recording member, a voice output member, service selection members respectively allocated to each life supporting service which is to be provided, wherein, as life supporting services are selected by operating corresponding ones of said service selection members, said image display member, said imagine member, said recording member and said voice output member get connected to service providing facilities which provide selected life supporting services through a telecommunications line or a computer network, and a data reader member which reads recorded data which are recorded in a recording medium from said recording medium, and is connected to service providing facilities which are selected by operating said service selection members so as to transmit said recorded data read from said recording medium to said service providing facilities to which said data reader member are connected.

5. The life supporting device of claim 4, further comprising:

a printing member which is connected to service providing facilities which are selected by operating said service selection members so as to print data contents which are transmitted from said service providing facilities to which said printing member are connected.

6. The life supporting device of claim 4, further comprising:

a vital data detection member which detects vital data and is connected to service providing facilities which are selected by operating said service selection members so as to transmit vital data, which are detected, to said service providing facilities to which said vital data detection member are connected.

7. The life supporting device of claim 4, further comprising:

a cursor movement control member which moves a cursor on a computer screen which is displayed on said display member.

8. The life supporting device of claim 4, wherein said service providing facilities include medical service facilities, and medical services are provided through said image display member, said imaging member, said recording member and said voice output member by means of connection with said medical service facilities.

9. The life supporting device of claim 4, wherein said service providing facilities include facilities which provide services regarding counseling.

10. The life supporting device of claim 4, wherein said service providing facilities include facilities which provide surrogate services for civic procedures.

11. The life supporting device of claim 4, wherein said service providing facilities include facilities which provide services as a travel agency.

12. The life supporting device of claim 4, wherein said service providing facilities include facilities which provide a service to introduce someone for conversation.

13. The life supporting device of claim 4, wherein said service providing facilities include facilities which provide the service of sending e-mail.

14. The life supporting device of claim 4, wherein said service providing facilities include facilities which provide the service of translating letters.

15. The life supporting device of claim 4, wherein said service providing facilities include facilities which provide the service of drawing composite sketches.

16. The life supporting device of claim 4, wherein said service providing facilities include facilities which provide game services.

17. The life supporting device of claim 4, wherein said service providing facilities include facilities which provide services regarding printed matter.

18. A life supporting device, comprising:

an image display member, an imaging member, a recording member, a voice output member, service selection members respectively allocated to each life supporting service which is to be provided, wherein as life supporting services are selected by operating corresponding ones of said service selection members, said image display member, said imaging member, said recording member and said voice output member get connected to service providing facilities which provide selected life supporting services through a telecommunications line or a computer network, and an image input member which scans and reads an image and is connected to service providing facilities which are selected by operating said service selection members so as to transmit image data which are read to said service providing facilities to which said image input member are connected.

19. A life supporting device, comprising:

an image display member, an imaging member, a recording member, a voice output member, and service selection members respectively allocated to each life supporting service which is to be provided, wherein as life supporting services are selected by operating corresponding ones of said service selection members, said image display member, said imaging member, said recording member and said voice output member get connected to service providing facilities which provide selected life supporting services through a telecommunications line or a computer network, wherein, a plurality of said service selection members are provided corresponding to each category of the life supporting services to be provided.

20. The life supporting device of claim 19, wherein said plurality of service selection members are colored differently from each other.

21. A life supporting device, comprising:

an image display member, an imaging member, a recording member, a voice output member, service selection members respectively allocated to each life supporting service which is to be provided, wherein, as life supporting services are selected by operating corresponding ones of said service selection members, said image display member, said imaging member, said recording member and said voice output member get connected to service providing facilities which provide selected life supporting services through a telecommunications line or a computer network, and a motion command member which performs image analysis on the motion of a person which is shot with said imaging member, compares thereof with previously set motion patterns, and outputs a predetermined operation signal, which corresponds to a motion pattern which matches with the captured motion of the person, to said imaging member, said recording member, said voice output member or said service selection members.

22. A life supporting device, comprising:

an image display member, an imaging member, a recording member, a voice output member, service selection members respectively allocated to each life supporting service which is to be provided, wherein as life supporting services are selected by operating corresponding ones of said service selection members, said image display member, said imaging member, said recording member and said voice output member get connected to service providing facilities which provide selected life supporting services through a telecommunications line or a computer network, and a voice command member which analyzes a voice which is recorded with said recording member, compares thereof with previously set voice patterns, and outputs a predetermined operation signal, which corresponds to a voice pattern which matches with the recorded voice, to said imaging member, said recording member, said voice output member or said service selection members.

23. A life supporting device, comprising:

an image display member, an imaging member, a recording member, a voice output member, service selection members respectively allocated to each life supporting service which is to be provided, wherein as life supporting services are selected by operating corresponding ones of said service selection members, said image display member, said imaging member, said recording member and said voice output member get connected to service providing facilities which provide selected life supporting services through a telecommunications line or a computer network, and an armrest member for supporting a human arm in front of an operation panel in which said image display member, said imaging member, said recording member, said voice output member and said service selection members are arranged.

24. A life supporting device, comprising:

an image display member, an imaging member, a recording member, a voice output member, service selection members respectively allocated to each life supporting service which is to be provided, wherein as life supporting services are selected by operating corresponding ones of said service selection members, said image display member, said imaging member, said recording member and said voice output member get connected to service providing facilities which provide selected life supporting services through a telecommunications line or a computer network, and an operation panel in which said image display member, said imaging member, said recording member, said voice output member and said service selection members are arranged disposed on a supportive base which is approximately as tall as a table.

* * * * *